(12) United States Patent
Jung et al.

(10) Patent No.: US 8,410,145 B2
(45) Date of Patent: Apr. 2, 2013

(54) INSECTICIDAL COMPOUNDS

(75) Inventors: Pierre Joseph Marcel Jung, Stein (CH); Peter Renold, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 92 days.

(21) Appl. No.: 12/808,847

(22) PCT Filed: Dec. 18, 2008

(86) PCT No.: PCT/EP2008/010863
§ 371 (c)(1),
(2), (4) Date: Jun. 17, 2010

(87) PCT Pub. No.: WO2009/077197
PCT Pub. Date: Jun. 25, 2009

(65) Prior Publication Data
US 2010/0273832 A1    Oct. 28, 2010

(30) Foreign Application Priority Data

Dec. 19, 2007 (GB) .................................... 0724757.0
May 9, 2008 (GB) .................................... 0808471.7

(51) Int. Cl.
*A61K 31/44* (2006.01)
*C07D 261/02* (2006.01)
(52) U.S. Cl. ......... 514/340; 514/378; 548/240; 548/127
(58) Field of Classification Search .................. 514/340, 514/378; 548/240, 127
See application file for complete search history.

(56) References Cited

U.S. PATENT DOCUMENTS
2008/0262057 A1 * 10/2008 Tisdell et al. ................. 514/378

FOREIGN PATENT DOCUMENTS

| EP | 1731512 | 12/2006 |
|---|---|---|
| EP | 1997813 | 12/2008 |
| JP | 2007308471 | 11/2007 |
| WO | 2007070606 | 6/2007 |
| WO | 2007105814 | 9/2007 |
| WO | 2008019760 | 2/2008 |
| WO | 2008126665 | 10/2008 |

* cited by examiner

*Primary Examiner* — Rei-tsang Shiao
(74) *Attorney, Agent, or Firm* — Brian D. McAlhaney

(57) ABSTRACT

A compound of formula (I): wherein $A^1$, $A^2$, $A^3$, $A^4$, $G^1$, $R^1$, $R^2$, $R^3$ and $R^4$ are as defined in claim 1; or a salt or N-oxide thereof. Furthermore, the present invention relates to processes and intermediates for preparing compounds of Formula (I), to insecticidal, acaricidal, molluscicidal or nematicidal compositions comprising them and to methods of using them to combat and control insect, acarine, mollusc or nematode pests.

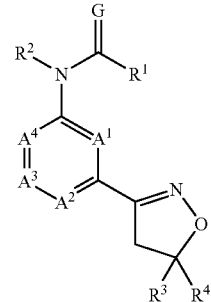

(I)

17 Claims, No Drawings

INSECTICIDAL COMPOUNDS

This application is a 371 of International Application No. PCT/EP2008/010863 filed Dec. 18, 2008, which claims priority to GB 0724757.0 filed Dec. 19, 2007, and GB 0808471.7 filed May 9, 2008, the contents of which are incorporated herein by reference.

The present invention relates to certain benzamide isoxazolines, to processes and intermediates for preparing them, to insecticidal, acaricidal, molluscicidal or nematicidal compositions comprising them and to methods of using them to combat and control insect, acarine, mollusc or nematode pests.

Certain isoxazoline derivatives with insecticidal properties are disclosed, for example, in EP 1,731,512, US 2007/066617, JP 2007/008914, JP 2007/016017, EP 1,932,836, JP 2007/106756, WO 07/070,606, EP 1,975,149 and WO 07/075,459.

It has now surprisingly been found that certain benzamide isoxazolines have insecticidal properties.

The present invention therefore provides a compound of formula (I)

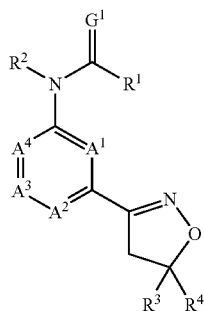

wherein
$A^1$, $A^2$, $A^3$ and $A^4$ are independently of one another C—H, C—$R^5$, or nitrogen, provided that no more than two of $A^1$, $A^2$, $A^3$ and $A^4$ are nitrogen;
$G^1$ is oxygen or sulfur;
$R^1$ is $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, $C_1$-$C_6$alkoxycarbonyl-, aryl-$C_1$-$C_6$alkyl- or aryl-$C_1$-$C_6$alkyl- substituted by one to three $R^6$, heterocyclyl-$C_1$-$C_6$alkyl- or heterocyclyl-$C_1$-$C_6$alkyl- substituted by one to three $R^6$; or
$R^1$ is aryl or aryl substituted by one to three $R^6$, or
$R^1$ is heterocyclyl or heterocyclyl substituted by one to three $R^6$;
$R^2$ is hydrogen, $C_1$-$C_6$alkyl, $C_1$-$C_6$alkylcarbonyl-, or $C_1$-$C_6$alkoxycarbonyl-;
$R^3$ is $C_1$-$C_6$haloalkyl;
$R^4$ is aryl or aryl substituted by one to three $R^7$, or heterocyclyl or heterocyclyl substituted by one to three $R^7$;
each $R^5$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl-;
each $R^6$ is independently halogen, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio-, $C_1$-$C_6$haloalkylthio-, $C_1$-$C_6$alkylsulfinyl-, $C_1$-$C_6$haloalkylsulfinyl-, $C_1$-$C_6$alkylsulfonyl-, $C_1$-$C_6$haloalkylsulfonyl-, or $C_1$-$C_6$alkoxycarbonyl-; and
each $R^7$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl-; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkylcarbonyl-, alkoxycarbonyl-) is a straight or branched chain and is, for example, methyl, ethyl, n-propyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups.

Halogen is fluorine, chlorine, bromine or iodine.

Haloalkyl groups (either alone or as part of a larger group, such as haloalkoxy) are alkyl groups which are substituted with one or more of the same or different halogen atoms and are, for example, trifluoromethyl, chlorodifluoromethyl, 2,2,2-trifluoroethyl, or 2,2-difluoroethyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Preferred heteroaryl groups are pyridyl, furanyl and thiadiazolyl, most preferably pyridyl. Examples of bicyclic groups include benzothiophenyl, benzimidazolyl, benzothiadiazolyl, quinolinyl, cinnolinyl and quinoxalinyl.

The term "heterocyclyl" is defined to include heteroaryl and in addition their unsaturated or partially unsaturated analogues.

Preferred values of $A^1$, $A^2$, $A^3$, $A^4$, $G^1$, $R^1$, $R^2$, $R^3$, $R^4$, $R^5$, $R^6$ and $R^7$ are, in any combination, as set out below.
Preferably $A^1$ is C—H or C—$R^5$, more preferably C—H or C—F, most preferably C—H.
Preferably $A^2$ is C—H or C—$R^5$, most preferably C—H.
Preferably $A^3$ is C—H or C—$R^5$, more preferably C—H or C—$CH_3$, most preferably C—H.
Preferably $A^4$ is C—H or C—$R^5$, more preferably C—H, C—F or C—CN, even more preferably C—F or C—CN, most preferably C—CN.

In one embodiment $A^1$, $A^2$, $A^3$ and $A^4$ are independently of one another C—H, C—$R^5$, or nitrogen, provided that only one of $A^1$, $A^2$, $A^3$ or $A^4$ is C—$R^5$, and the other $A^1$, $A^2$, $A^3$ and $A^4$ are C—H or nitrogen.

In one embodiment $A^1$, $A^2$, $A^3$ and $A^4$ are independently of one another C—H, C—CN, or nitrogen, provided that only one of $A^1$, $A^2$, $A^3$ or $A^4$ is C—CN, and the other $A^1$, $A^2$, $A^3$ and $A^4$ are C—H or nitrogen.

In one embodiment $A^1$, $A^2$, $A^3$ and $A^4$ are independently of one another C—H or C—CN, provided that only one of $A^1$, $A^2$, $A^3$ or $A^4$ is C—CN, and the other $A^1$, $A^2$, $A^3$ and $A^4$ are C—H.

Preferably $G^1$ is oxygen.

$R^1$ is preferably $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, aryl-$C_1$-$C_6$alkyl- or aryl-$C_1$-$C_6$alkyl- substituted by one to three $R^6$, aryl or aryl substituted by one to three $R^6$, or heterocyclyl or heterocyclyl substituted by one to three $R^6$, more preferably $C_1$-$C_6$alkyl, $C_1$-$C_5$haloalkoxy, aryl or aryl substituted by one to three $R^6$, or heteroaryl or heteroaryl substituted by one to three $R^6$, most preferably $C_1$-$C_6$allyl, $C_1$-$C_6$haloalkoxy, aryl or aryl substituted by one to three $R^6$, or pyridyl, furanyl or thiadiazolyl or pyridyl, furanyl or thiadiazolyl substituted by one to three $R^6$.

In one group of preferred compounds $R^1$ is $C_1$-$C_6$alkyl, $C_1$-$C_6$haloalkyl, $C_1$-$C_3$alkoxy-$C_1$-$C_3$ alkyl-, $C_1$-$C_6$alkoxy, $C_1$-$C_6$haloalkoxy, $C_1$-$C_6$alkoxycarbonyl-, aryl-$C_1$-$C_6$alkyl- or aryl-$C_1$-$C_6$alkyl- substituted by one to three $R^6$, heterocyclyl-$C_1$-$C_6$alkyl- or heterocyclyl-$C_1$-$C_6$allyl- substituted by one to three $R^6$, more preferably $C_1$-$C_6$alkyl, $C_1$-$C_6$haloallyl, $C_1$-$C_3$alkoxy-$C_1$-$C_3$alkyl-, $C_1$-$C_6$alkoxy, $C_1$-$C_6$haloalkoxy, aryl-$C_1$-$C_6$alkyl- or aryl-$C_1$-$C_6$alkyl-substituted by one to three $R^6$, most preferably n-butyl, bromomethyl, methoxymethyl-, 2,2,2-trichloro-ethoxy, or 4-chloro-benzyl-.

In one group of preferred compounds $R^1$ is aryl or aryl substituted by one to three $R^6$, more preferably $R^1$ is aryl or aryl substituted by one to three $R^6$, most preferably $R^1$ is 2-chloro-4-cyano-phenyl, 2-chloro-4-fluoro-phenyl-, 5-chloro-2-fluoro-phenyl-, 2-chloro-4-nitro-phenyl-, 2-chloro-phenyl-, 4-cyano-phenyl-, 4-cyano-2-methyl-phenyl-, 2,3-difluoro-phenyl-, 2,4-difluoro-phenyl-, 4-fluoro-2-methyl-phenyl-, 2-fluoro-phenyl-, 4-fluoro-phenyl-, 2-fluoro-5-trifluoromethyl-phenyl-, 4-fluoro-3-trifluoromethyl-phenyl-, 2-methoxy-phenyl-, 2-methyl-phenyl-, 4-methyl-phenyl-, 2-methyl-3-nitro-phenyl-, 2-methylthio-phenyl, 4-nitro-phenyl-, phenyl-, 2-trifluoromethoxy-phenyl-, 4-trifluoromethoxy-phenyl-, 2-trifluoromethyl-phenyl-, or 4-trifluoromethyl-phenyl-.

In another group of preferred compounds $R^1$ is heterocyclyl or heterocyclyl substituted by one to three $R^6$, more preferably $R^1$ is heteroaryl or heteroaryl substituted by one to three $R^6$, even more preferably $R^1$ is pyridyl or pyridyl substituted by one to three $R^6$. Further examples of preferred groups for $R^1$ include furan-2-yl-, and 4-methyl-[1,2,3]thiadiazol-5-yl-.

Preferably $R^2$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^3$ is chlorodifluoromethyl or trifluoromethyl, most preferably trifluoro-methyl.

In one group of preferred compounds $R^4$ is aryl or aryl substituted by one to three $R^7$, more preferably $R^4$ is phenyl or phenyl substituted by one to three $R^7$, even more preferably $R^4$ is 3,5-dibromo-phenyl, 3,5-dichloro-phenyl, 3,4-dichloro-phenyl, or 3,4,5-trichloro-phenyl, most preferably $R^4$ is 3,5-dichloro-phenyl.

In another preferred group of compounds $R^4$ is heterocyclyl or heterocyclyl substituted by one to three $R^7$, more preferably $R^4$ is heteroaryl or heteroaryl substituted by one to three $R^7$, most preferably $R^4$ is pyridyl or pyridyl substituted by one to three $R^7$.

Preferably each $R^5$ is independently bromo, chloro, fluoro, cyano, nitro, methyl, ethyl, trifluoromethyl, methoxy, difluoromethoxy, trifluoromethoxy, or methoxycarbonyl-, more preferably bromo, chloro, fluoro, cyano, nitro, or methyl, most preferably chloro, fluoro, cyano, or methyl.

Preferably each $R^6$ is independently halogen, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio-, or $C_1$-$C_6$haloalkylthio-, most preferably chloro, fluoro, cyano, nitro, methyl, trifluoromethyl, methoxy, trifluoromethoxy, methylthio-, or trifluoromethylthio-.

Preferably each $R^7$ is independently bromo, chloro, fluoro, cyano, nitro, methyl, ethyl, trifluoromethyl, methoxy, difluoromethoxy, trifluoromethoxy, or methoxycarbonyl-, more preferably bromo, chloro, or fluoro, most preferably chloro.

A preferred embodiment are compounds of formula (Ia) wherein $G^1$, $R^1$ and $R^2$ are as defined for a compound of formula (I) and $R^3$ is trifluoromethyl, $R^4$ is 3,5-dichloro-phenyl, and $A^1$, $A^2$, $A^3$, and $A^4$ are C—H; or a salt or N-oxide thereof.

A preferred embodiment are compounds of formula (Ib) wherein $G^1$, $R^1$ and $R^2$ are as defined for a compound of formula (I) and $R^3$ is trifluoromethyl, $R^4$ is 3,5-dichloro-phenyl, $A^1$ is C—F, and $A^2$, $A^3$, and $A^4$ are C—H; or a salt or N-oxide thereof.

A preferred embodiment are compounds of formula (Ic) wherein $G^1$, $R^1$ and $R^2$ are as defined for a compound of formula (I) and $R^3$ is trifluoromethyl, $R^4$ is 3,5-dichloro-phenyl, $A^1$, $A^2$, and $A^3$, are C—H, and $A^4$ is C—F; or a salt or N-oxide thereof.

A preferred embodiment are compounds of formula (Id) wherein $G^1$, $R^1$ and $R^2$ are as defined for a compound of formula (I) and $R^3$ is trifluoromethyl, $R^4$ is 3,5-dichloro-phenyl, $A^1$, $A^2$, and $A^3$, are C—H, and $A^4$ is C—CN; or a salt or N-oxide thereof.

A preferred embodiment are compounds of formula (Ie) wherein $G^1$, $R^1$ and $R^2$ are as defined for a compound of formula (I) and $R^3$ is trifluoromethyl, $R^4$ is 3,5-dichloro-phenyl, $A^1$, $A^2$, and $A^4$, are C—H, and $A^3$ is C-Me; or a salt or N-oxide thereof.

A further embodiment of this invention are compounds of formula (I') wherein $A^1$, $A^2$, $A^3$ and $A^4$ are independently of one another C—H, C—$R^5$, or N;
$G^1$ is oxygen or sulfur;
$R^1$ is $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, $C_1$-$C_6$alkoxycarbonyl, aryl-$C_1$-$C_6$alkyl- or aryl-$C_1$-$C_6$alkyl- substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, heterocyclyl-$C_1$-$C_6$alkyl- or heterocyclyl-$C_1$-$C_6$alkyl- substituted by one to three substituents independently selected from halogen, cyano, nitro, $C_1$-$C_6$alkyl, $C_1$-$C_6$haloallyl, $C_1$-$C_6$alkoxy, $C_1$-$C_6$haloalkoxy, or $C_1$-$C_6$alkoxycarbonyl; or
$R^1$ is aryl or aryl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or
$R^1$ is heterocyclyl or heterocyclyl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl;
$R^2$ is hydrogen, $C_1$-$C_6$alkyl, $C_1$-$C_6$alkylcarbonyl, or $C_1$-$C_6$alkoxycarbonyl;
$R^3$ is $C_1$-$C_6$halo alkyl;
$R^4$ is aryl or aryl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or heterocyclyl or heterocyclyl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; and
each $R^5$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; or a salt or N-oxide thereof. The preferences for $A^1$, $A^2$, $A^3$, $A^4$, $G^1$, $R^1$, $R^2$, $R^3$, $R^4$, and $R^5$ are the same as the preferences set out for the corresponding substituents of compounds of the formula (I).

A further embodiment of this invention are compounds of formula (I") wherein $A^1$, $A^2$, $A^3$ and $A^4$ are independently of one another C—H, C—$R^5$, or nitrogen, provided that no more than two of $A^1$, $A^2$, $A^3$ and $A^4$ are nitrogen;
$G^1$ is oxygen or sulfur;
$R^1$ is $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, $C_1$-$C_6$alkoxycarbonyl, aryl-$C_1$-$C_6$alkyl- or aryl-$C_1$-$C_6$alkyl- substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, heterocyclyl-$C_1$-$C_6$alkyl- or heterocyclyl-$C_1$-$C_6$alkyl- substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; or $R^1$ is aryl or aryl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or $R^1$ is heterocyclyl or heterocyclyl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl;

$R^2$ is hydrogen, $C_1$-$C_6$alkyl, $C_1$-$C_6$alkylcarbonyl, or $C_1$-$C_6$alkoxycarbonyl;

$R^3$ is $C_1$-$C_6$haloalkyl;

$R^4$ is aryl or aryl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl, or heterocyclyl or heterocyclyl substituted by one to three substituents independently selected from halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; and each $R^5$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl; or a salt or N-oxide thereof. The preferences for $A^1$, $A^2$, $A^3$, $A^4$, $G^1$, $R^1$, $R^2$, $R^3$, $R^4$, and $R^5$ are the same as the preferences set out for the corresponding substituents of compounds of the formula (I).

The compounds in Table 1 to Table 5 below illustrate the compounds of the invention.

TABLE 1

Table 1 provides 25 compounds of formula (Ia) wherein $R^1$ has the values listed in the table below

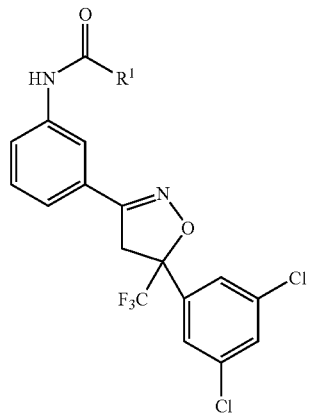

(Ia)

| Compound numbers | $R^1$ |
|---|---|
| 1.01 | 2-chloro-4-fluoro-phenyl- |
| 1.02 | 5-chloro-2-fluoro-phenyl- |
| 1.03 | 2-chloro-4-nitro-phenyl- |
| 1.04 | 2-chloro-phenyl- |
| 1.05 | 4-cyano-phenyl- |
| 1.06 | 4-cyano-2-methyl-phenyl- |
| 1.07 | 2,3-difluoro-phenyl- |
| 1.08 | 2,4-difluoro-phenyl- |
| 1.09 | 4-fluoro-2-methyl-phenyl- |
| 1.10 | 2-fluoro-phenyl- |

TABLE 1-continued

Table 1 provides 25 compounds of formula (Ia) wherein $R^1$ has the values listed in the table below

| Compound numbers | $R^1$ |
|---|---|
| 1.11 | 4-fluoro-phenyl- |
| 1.12 | 2-fluoro-5-trifluoromethyl-phenyl- |
| 1.13 | 4-fluoro-3-trifluoromethyl-phenyl- |
| 1.14 | furan-2-yl- |
| 1.15 | 2-methoxy-phenyl- |
| 1.16 | 2-methyl-phenyl- |
| 1.17 | 4-methyl-phenyl- |
| 1.18 | 4-methyl-[1,2,3]thiadiazol-5-yl- |
| 1.19 | 2-methyl-3-nitro-phenyl- |
| 1.20 | 4-nitro-phenyl- |
| 1.21 | phenyl- |
| 1.22 | 2-trifluoromethoxy-phenyl- |
| 1.23 | 4-trifluoromethoxy-phenyl- |
| 1.24 | 2-trifluoromethyl-phenyl- |
| 1.25 | 4-trifluoromethyl-phenyl- |

TABLE 2

Table 2 provides 25 compounds of formula (Ib) wherein $R^1$ has the values listed in Table 1.

(Ib)

TABLE 3

Table 3 provides 25 compounds of formula (Ic) wherein $R^1$ has the values listed in Table 1.

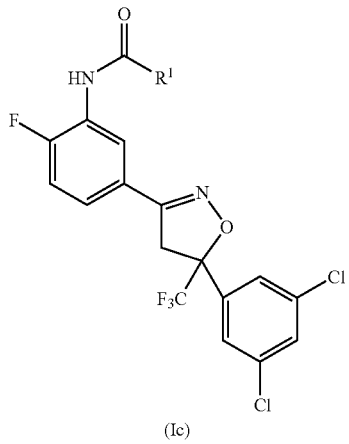

(Ic)

TABLE 4

Table 4 provides 25 compounds of formula (Id) wherein $R^1$ has the values listed in Table 1.

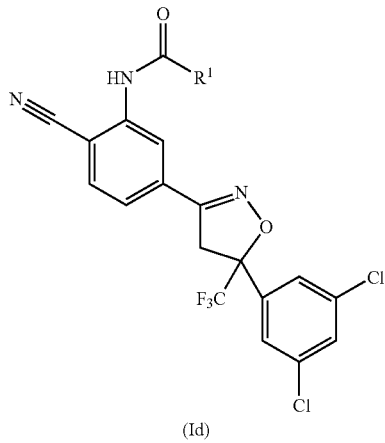

(Id)

TABLE 5

Table 5 provides 25 compounds of formula (Ie) wherein $R^1$ has the values listed in Table 1.

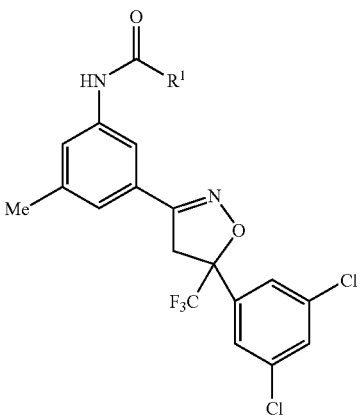

(Ie)

The compounds of the invention may be made by a variety of methods as shown in Scheme 1 to Scheme 5.

1) Compounds of formula (I) wherein $G^1$ is oxygen, can be made by treatment of a compound of formula (II) with an acid derivative of formula $RC(O)R^1$ as shown in Scheme 1.

Scheme 1

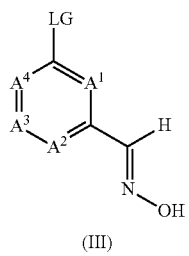

(III)

1. halogenating agent
2. $R^3$ ＝ $CH_2$ / $R^4$ (VII)

base

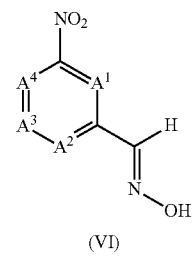

(VI)

1. halogenating agent
2. $R^3$ ＝ $CH_2$ / $R^4$ (VII)

base

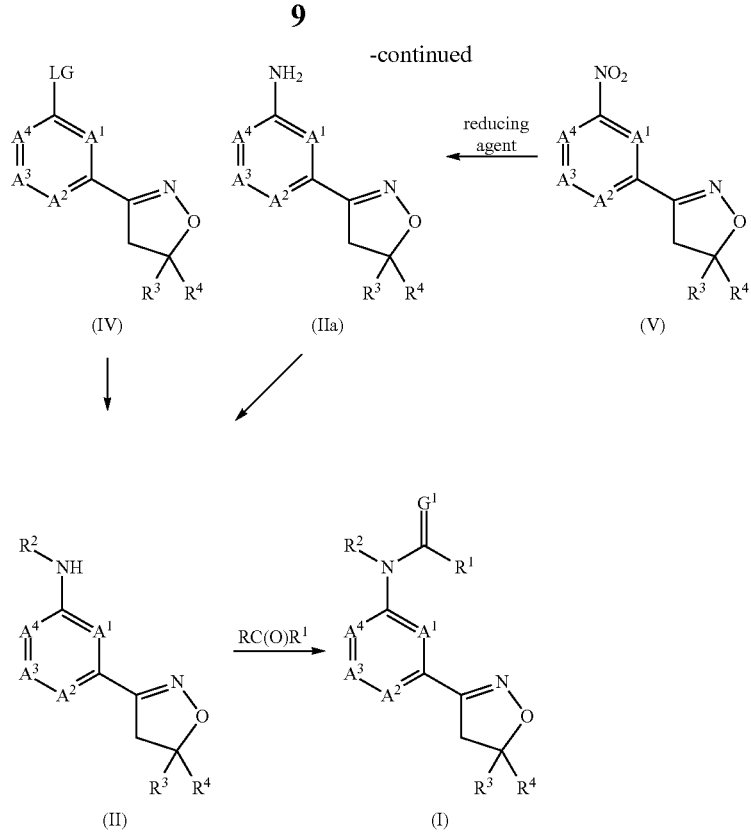

When R is OH such reactions are usually carried out in the presence of a coupling reagent, such as N,N'-dicyclohexyl-carbodiimide ("DCC"), 1-ethyl-3-(3-dimethylamino-propyl)-carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Acid derivatives of formula RC(O)$R^1$ are commercially available or can be made by methods known to a person skilled in the art.

2) Compounds of formula (II) can be made from a compound of formula (IIa) by formation of the N—$R^2$ bond. It is known to a person skilled in the art that there are many reported methods for the formation of this bond depending on the nature of the substituent $R^2$. For example, reductive amination may be achieved by treatment of the primary amine with an aldehyde or ketone and a reducing agent such as sodium cyanoborohydride. Alternatively, alkylation may be achieved by treating the primary amine with an alkylating agent such as an alkyl halide, optionally in the presence of a base. Alternatively, arylation may be achieved by treatment of the primary amine with an aryl halide or sulfonate in the presence of a suitable catalyst/ligand system, often a palladium(0) complex.

3) Alternatively, compounds of formula (II) can be made from a compound of formula (IV), wherein LG is a leaving group, such as fluoro, chloro or a sulfonate, via nucleophilic displacement of the leaving group by an amine of formula $R^2$—$NH_2$. Similar reactions have been described in, for example, Bioorganic & Medicinal Chemistry (2006), 14(13), 4361-4372. Amines of formula $R^2$—$NH_2$ are commercially available or can be made by known methods known to a person skilled in the art.

4) Compounds of formula (IIa) can be made by treatment of a compound of formula (V) with a reducing agent. There are numerous methods for achieving such a transformation reported in the literature, such as treatment with tin(II) chloride under acidic conditions, or hydrogenation catalyzed by a noble metal such as palladium on carbon. A preferred solvent is isopropanol. The reaction is carried out at a temperature of from 0° C. to 200° C., preferably from 50° C. to 150° C., in particular at 80° C.

5) Compounds of formula (V) can be made by reaction of an oxime of formula (VI) and a vinyl compound of formula (VII) in a two step reaction. In the first step, the oxime of formula (VI) is reacted with a halogenating agent, for example a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

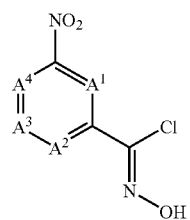

(VI')

In the second step, the chloro hydroxy imine intermediate of formula (VI') is reacted with the vinyl compound of formula (VII) in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the chloro hydroxy imine intermediate or more conveniently to conduct these two steps successively in one reaction vessel without isolation of the intermediate. The second step is carried out at a temperature of from 0° C. to 100° C., preferably from 15° C. to 30° C., in particular at ambient temperature. Hydroxyl-oximes of formula (VI) are commercially available or can be made by methods known to a person skilled in the art. Vinyl compounds of formula (VII) are commercially available or can be made as described in Scheme 5 or by methods known to a person skilled in the art. Similar procedures are known, for example, from Indian Journal of Chemistry, Section B (1993), 32B(4), 471-474; and Current Organic Chemistry (2005), 9(10), 925-958.

6) Similarly, compounds, of formula (IV) wherein LG is a leaving group, such as fluoro, chloro or a sulfonate, can be made by reaction of an oxime of formula (III) wherein LG is a leaving group, such as fluoro, chloro or a sulfonate, and a vinyl compound of formula (VII) in a two step reaction using the reaction conditions as described under 5). The intermediate of formula (III') wherein LG is a leaving group, such as fluoro, chloro or a sulfonate, can optionally be isolated.

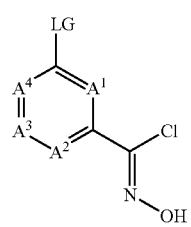

(III')

Hydroxyl-oximes of formula (III) are commercially available or can be made by methods known to a person skilled in the art.

7) Compounds of formula (I) wherein $G^1$ is sulfur, can be made from a compound of formula (I) wherein $G^1$ is oxygen, by treatment with a thio-transfer reagent, such as Lawesson's reagent or phosphorus pentasulfide.

8) Compounds of formula (V) wherein $R^3$ is cyano, can be made from a compound of to formula (V') wherein LG is halogen, such as fluoride or chloride, by reaction with a cyanide salt, such as potassium cyanide, optionally in the presence of a base, such as potassium carbonate.

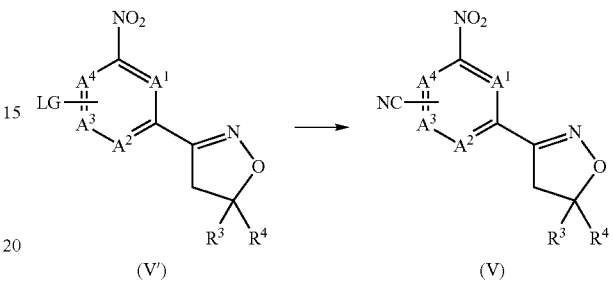

The presence of the nitro group facilitates the displacement of the leaving group by the cyanide ion.

9) Compounds of formula (IIa) wherein $R^3$ is cyano, can be made from a compound of formula (IIa') wherein LG is halogen, such as bromide or iodide, by reaction with a cyanide salt, such as copper(I) cyanide or zinc(II) cyanide, optionally in the presence of a palladium catalyst, such as tetrakis(triphenylphosphine)palladium(0, and optionally in the presence of a metal halide, such as copper(I) iodide or zinc(II) iodide, in suitable solvent such N,N-dimethylformamide or N-methylpyrrolidine). The reaction is carried out at a temperature of from 0° C. to 200° C., preferably from 50° C. to 150° C., in particular at 100° C.

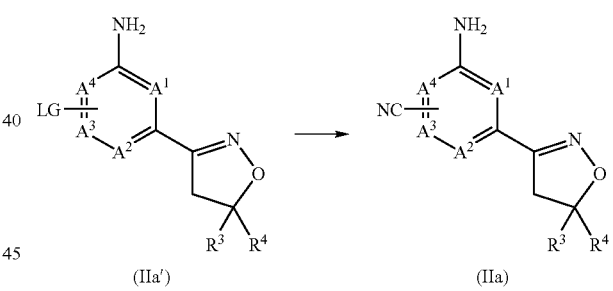

Similar reactions with copper(I) cyanide have been described in, for example, J. Med. Chem. (2004), 47(8), 1969-1986, J. Med. Chem. (2002), 45(17), 3692-3702 and J. Med. Chem. (1989), 32(3), 575-83. Similar reactions with zinc(II) cyanide in the presence of a palladium catalyst have been described in, for example, Bioorganic & Medicinal Chemistry Letters (2007), 17(7), 1908.

Scheme 2

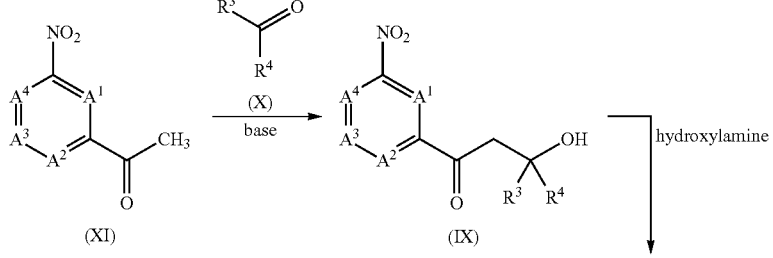

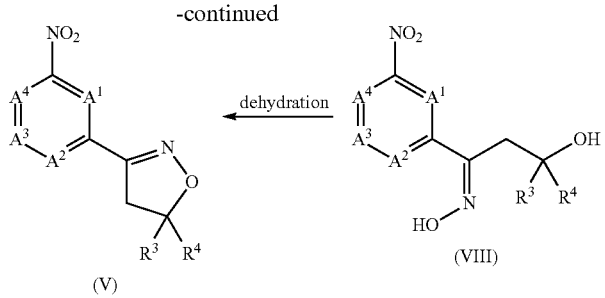

10) Alternatively, compounds of formula (V) can be prepared by cyclisation of a compound of formula (VIII), as shown in Scheme 2. The cyclisation of a compound of formula (VIII) can also be referred to as the dehydration of a compound of formula (VIII). Such reactions are usually carried out in the presence of an acid, for example an inorganic acid, such as hydrochloric acid or sulfuric acid, or a sulfonic acid, such as methanesulfonic acid, optionally in a solvent such as water, ethanol or tetrahydrofuran, or mixtures thereof. The reaction is carried out at a temperature of from 0° C. to 100° C., preferably from 40° C. to 80° C. Representative experimental conditions for this transformation are described in Synthetic Communications 2003, 23, 4163-4171. Alternatively, dehydration can be carried out using a dehydrating agent, such as phosphorus pentoxide, in a solvent, such as chloroform, at a temperature of from −20° C. to +50°, preferably at 0° C., as described in Journal of Heterocyclic Chemistry 1990, 27, 275. Alternatively, cyclisation can be carried out under Mitsonobu conditions involving treatment of a compound of formula (VIII) with a phosphine, such as triphenylphosphine, and an azodicarboxylate reagent, such as diethyl azodicarboxylate, diisopropyl azodicarboxylate or dicyclohexyl azodicarboxylate, in a solvent, such as tetrahydrofuran, at a temperature of from 0° C. to 80° C., preferably from 0° C. to ambient temperature.

11) Compounds of formula (VIII) can be made by reaction of a β-hydroxy ketone of formula (IX) with a hydroxylamine, such as hydroxylamine hydrochloride. Such reactions are carried out optionally in the presence of a base, for example an organic base, such as triethylamine or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature.

12) Compounds of formula (IX), can be made by aldol-type reaction of a methyl ketone of formula (XI) with a ketone of formula (X). Such reactions are usually carried out in the presence of a base, such as sodium hydride, lithium hydride, lithium diisopropylamide or lithium hexamethyldisilazide, in a solvent, such as tetrahydrofuran, at a temperature of from −78° C. to +100° C., preferably from 0° C. to +80° C. Alternatively, the reaction can be performed using a Lewis acid, such as titanium tetrachloride, and an amine, such as triethylamine, diisopropylethylamine, tetramethylethylenediamine ("TMEDA") or tributylamine, in a solvent, such as dichloromethane, at a temperature of from −78° C. to ambient temperature, preferably at −78° C. Representative conditions for such a transformation are given in Tetrahedron Letters 1997, 38, 8727-8730. Methyl ketones of formula (XI), for example 5-acetyl-2-nitrobenzonitrile (CAS RN 223726-10-1 as known from Organometallics (1999), 18(8), 1562-1564), are commercially available or can be made by methods known to a person skilled in the art. Ketones of formula (X) are commercially available or can be made by methods known to a person skilled in the art.

Scheme 3

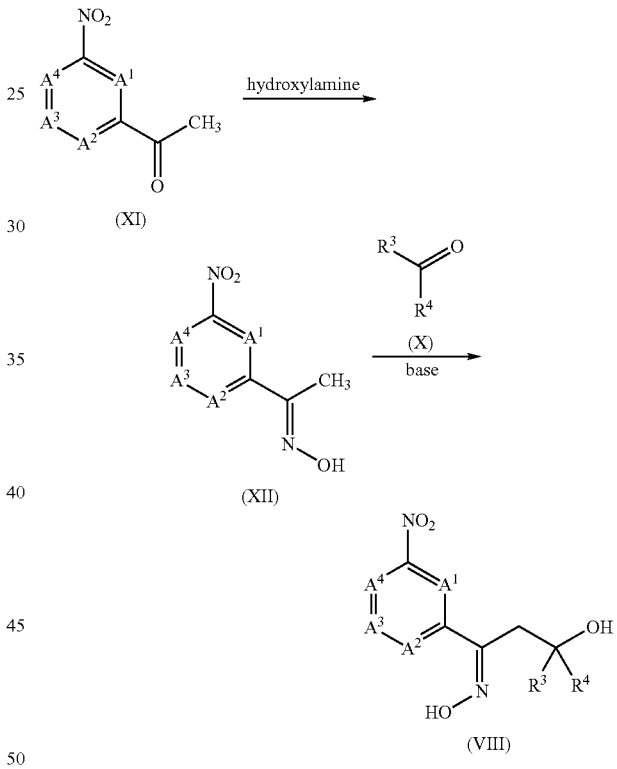

13) Alternatively, compounds of formula (VIII) can be prepared by reacting a methyl oxime of formula (XII) with a ketone of formula (X) in an aldol-type reaction as shown in Scheme 3. Such reactions are usually carried out by treating the methyl oxime of formula (XII) with a base, such as n-butyl lithium, lithium diisopropylamide or lithium hexamethyldisilazide, in a solvent, such as tetrahydrofuran, at a temperature of from −78° C. to ambient temperature, preferably from −20° C. to 0° C., followed by addition of the ketone of formula (X) at a temperature of from −78° C. to 0° C., preferably at 0° C. Representative conditions for such a transformation can be found in Synthetic Communications 2003, 23, 4163-4171.

14) Compounds of formula (XII) can be made by reaction of a methyl ketone of formula (XI) with a hydroxylamine as described under 11). Methyl ketones of formula (XI), for example 5-acetyl-2-nitrobenzonitrile (CAS RN 223726-10-1 as known from Organometallics (1999), 18(8), 1562-1564), are commercially available or can be made by methods known to a person skilled in the art.

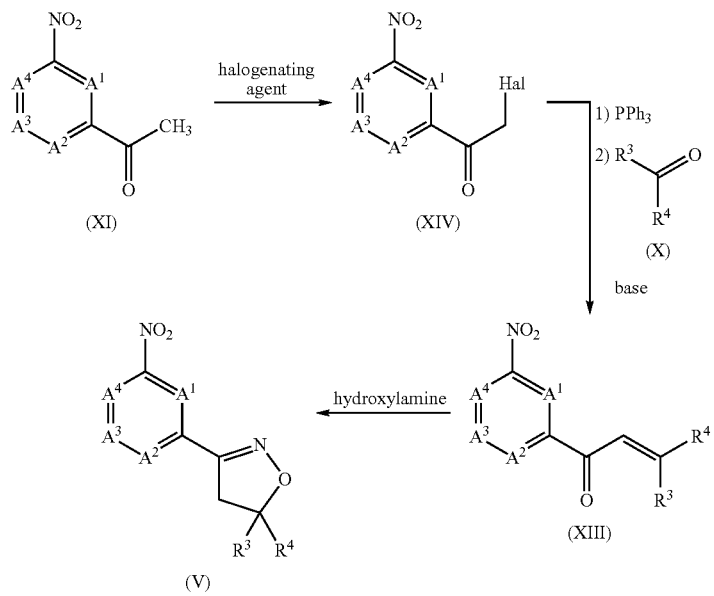

Scheme 4

15) Alternatively, compounds of formula (V) can be obtained by reacting an unsaturated ketone of formula (XIII) with a hydroxylamine, such as hydroxylamine hydrochloride, as shown on Scheme 4. Such reactions can be performed optionally in the presence of a base, such as sodium hydroxide or potassium hydroxide, in a solvent, such as methanol, ethanol or water, or mixtures thereof, at a temperature of from 0° C. to 100° C., preferably from ambient temperature to 80° C. Such conditions are described, for example, in J. Indian Chemical Society 1988, 65(9), 640-2. Such reactions may optionally lead to intermediates of formula (XIII')

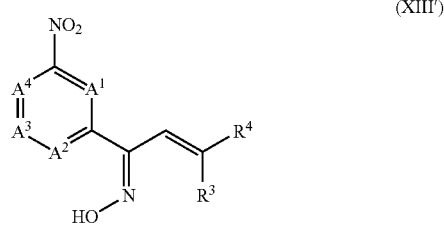

(XIII')

Such intermediates can be converted into compounds of formula (I) in the presence of an acid, such as hydrochloric acid or acetic acid, or mixtures thereof, or a base, such as sodium methoxide, optionally in a solvent, such as methanol or diethyl ether, at a temperature of from 0° C. to 100° C. Representative procedures for this reaction are described in Eur. J. Org. Chem. 2002, p 1919.

16) Compounds of formula (XIII) can be obtained by various methods. For example, they can be prepared by reacting in a first step a compound of formula (XIV) wherein Hal is a halogen, such as bromo or chloro, with a phosphine, such as triphenylphosphine. Such reactions are usually performed in a solvent, such as toluene, at a temperature of from ambient temperature to 150° C., preferably from 80° C. to 120° C. In a second step, the intermediate is treated with a ketone of formula (X) and a base, such as n-butyl lithium or triethylamine, in a solvent, such as tetrahydrofuran, at a temperature of from −78° C. to +100° C., preferably from ambient temperature to +80° C. Such conditions are described, for example, in Journal of Organic Chemistry 2006, 71(9), 3545-3550.

17) Compounds of formula (XIV) wherein Hal is a halogen, such as bromo or chloro, can be prepared by reacting a methyl ketone of formula (XI) with a halogenating agent, such as bromine or chlorine, in a solvent, such as acetic acid, at a temperature of from 0° C. to 50° C., preferably from ambient temperature to 40° C. Methyl ketones of formula (XI), for example 5-acetyl-2-nitrobenzonitrile (CAS RN 223726-10-1 as known from Organometallics (1999), 18(8), 1562-1564), are commercially available or can be made by methods known to a person skilled in the art.

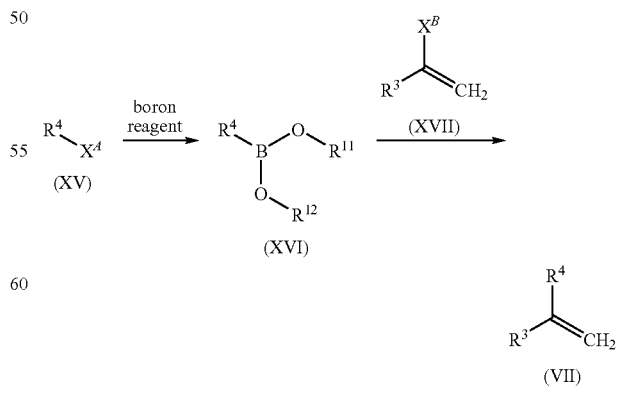

Scheme 5

18) Vinyl compounds of formula (VII) can be made from a compound of formula (XV) wherein $X^4$ is a leaving group such as a halogen, preferably bromine, in a two step process as shown in Scheme 5. First a compound of formula (XV), wherein $R^4$ is phenyl, substituted phenyl, heterocyclyl or substituted heterocyclyl, is reacted with a boron reagent of the formula $[B(OR^{11})(OR^{12})]_2$ wherein $R^{11}$ and $R^{12}$ are independently hydrogen, $C_1$-$C_6$alkyl or $C_1$-$C_6$haloalkyl, or $R^{11}$ and $R^{12}$ together with the two oxygen atoms and the boron atom through which they are connected form a five to seven-membered heterocyclyl ring, which can optionally be substituted by one to eight $C_1$-$C_4$alkyl or $C_1$-$C_4$haloalkyl groups, such as bis(pinacolato)diboron, in the presence of a catalyst/ligand system, often a palladium(II) complex, in the presence of a base under an inert atmosphere. Such procedures are known, for example, from Palladium(0)-Catalyzed Cross-Coupling Reaction of Alkoxydiboron with Haloarenes: A Direct Procedure for Arylboronic Esters; Ishiyama, Tatsuo; Murata, Miki; Miyaura, Norio; and Journal of Organic Chemistry (1995), 60(23), 7508-10. Then boronic ester of formula (XVI) is then reacted with a vinyl halide of formula (XVII) in the presence of a suitable catalyst/ligand system, often a palladium(II) complex, in the presence of a base under an inert atmosphere. Such procedures are known, for example, from WO 02/08221. Vinyl halides of formula (XVII) are commercially available or can be made by methods known to a person skilled in the art.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogen carbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole (Rynaxypyr®) or cyantraniliprole;

t) Sulfoxaflor; or u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrroInitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 4-bromo-3-nitro-benzaldehyde oxime

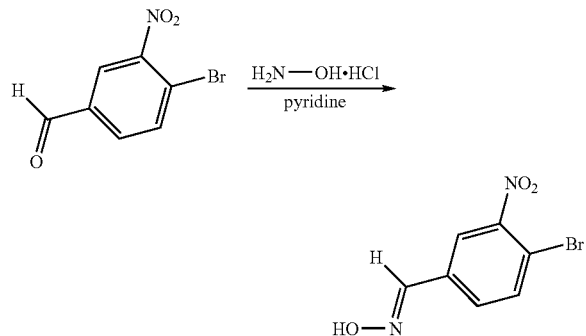

To a solution of 4-bromo-3-nitro-benzaldehyde (commercially available) (10 g, 43.5 mmol) in methanol (28 ml) under a nitrogen atmosphere was added pyridine (7.74 g, 97.8 mmol) and hydroxylamine hydrochloride (6.04 g, 86.94 mmol). The reaction mixture was stirred at ambient temperature for 16 hours. The reaction mixture was diluted with a mixture of ethyl acetate and aqueous sodium hydrogen carbonate (saturated). The phases were separated and the aqueous phase was extracted twice with ethyl acetate. The combined organic phases were dried over sodium sulfate and concentrated. The residue was purified by column chromatography on silica gel (eluent: ethyl acetate/cyclohexane 1:3) to give 4-bromo-3-nitro-benzaldehyde oxime (5.34 g, 67% yield). $^1$H-NMR (CDCl$_3$, 400 MHz): 8.11 (s, 1H), 8.05 (d, 1H), 7.75 (d, 1H), 7.62 (m, 2H).

4-Fluoro-3-nitro-benzaldehyde oxime was made from 4-fluoro-3-nitro-benzaldehyde (commercially available) using an analogous procedure. $^1$H-NMR (CDCl$_3$, 400 MHz): 8.26 (m, 1H), 8.12 (s, 1H), 8.04 (s, 1H), 7.87 (m, 1H), 7.3 (t, 1H).

3-Methyl-5-nitro-benzaldehyde oxime was made from 3-methyl-5-nitro-benzaldehyde (which was made as described, for example, in U.S. Pat. No. 4,634,705) using an analogous procedure. $^1$H-NMR (CDCl$_3$, 400 MHz): 8.5 (s, 1H), 8.25 (s, 1H), 8.20 (s, 1H), 8.04 (s, 1H), 7.71 (s, 1H), 2.48 (s, 3H).

2-Fluoro-3-nitro-benzaldehyde oxime was made from 2-fluoro-3-nitro-benzaldehyde (commercially available) using an analogous procedure. $^1$H-NMR (CDCl$_3$, 400 MHz): 8.43 (s, 1H), 8.09 (m, 3H), 7.34 (t, 1H).

Example I2

Preparation of 5-(3,5-dichloro-phenyl)-3-(3-nitro-phenyl)-5-trifluoromethyl-4,5-dihydro-isoxazole

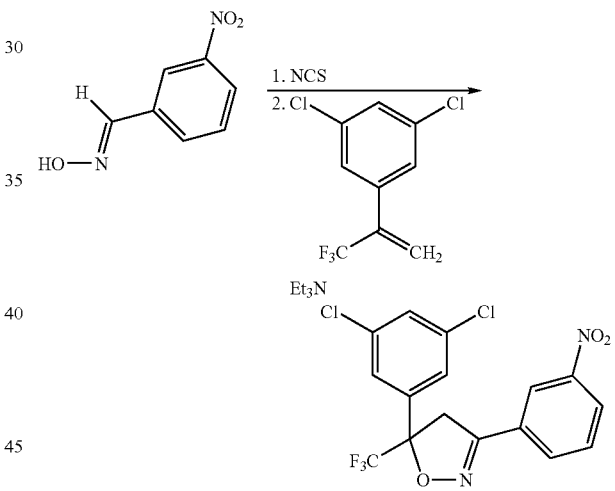

3-Nitro-benzaldehyde oxime (commercially available) (6.15 g, 37.0 mmol) and N-chlorosuccinimide ("NCS") (4.94 g, 37.0 mmol) were dissolved in N,N-dimethylformamide (65 ml). This mixture was stirred at ambient temperature for 90 minutes. A solution of 1,3-dichloro-5-(1-trifluoromethyl-vinyl)-benzene (which was made as described, for example, in WO 05/085216) (8.53 mg, 37.0 mmol) and triethylamine (5.15 ml, 37.0 mmol) in N,N-dimethylformamide (70 ml) was added and the reaction mixture was stirred at ambient temperature for 18 hours. Water (300 ml) and ethyl acetate (300 ml) were added. The phases were separated and the organic phase was washed twice with water. The aqueous phases were extracted with ethyl acetate. The combined organic phases were dried over sodium sulfate and concentrated. The residue was purified by column chromatography on silica gel (eluent: cyclohexane/ethyl acetate 2:1) to give 5-(3,5-dichloro-phenyl)-3-(3-nitro-phenyl)-5-trifluoromethyl-4,5-dihydro-isoxazole (14.5 g, 97% yield). The residue was used without further purification or analysis.

5-(3,5-Dichloro-phenyl)-3-(4-bromo-3-nitro-phenyl)-5-trifluoromethyl-4,5-dihydro-isoxazole was made from 4-bromo-3-nitro-benzaldehyde oxime (Example I1) using an analogous procedure and was purified by column chromatography on silica gel (eluent: cyclohexane/ethyl acetate 3:1). $^1$H-NMR (CDCl$_3$, 400 MHz): 8.07 (s, 1H), 7.78 (m, 2H), 7.48 (s, 2H), 7.42 (s, 1H), 4.11 (d, 1H), 3.72 (d, 1H).

5-(3,5-Dichloro-phenyl)-3-(4-fluoro-3-nitro-phenyl)-5-trifluoromethyl-4,5-dihydro-isoxazole was made from 4-fluoro-3-nitro-benzaldehyde oxime (Example I1) using an analogous procedure and was purified by column chromatography on silica gel (eluent: cyclohexane/ethyl acetate 3:1). $^1$H-NMR (CDCl$_3$, 400 MHz): 8.27 (q, 1H), 8.05 (m, 1H), 7.50 (m, 2H), 7.40 (m, 2H), 4.12 (d, 1H), 3.75 (d, 1H).

5-(3,5-Dichloro-phenyl)-3-(3-methyl-5-nitro-phenyl)-5-trifluoromethyl-4,5-dihydro-isoxazole was made from 3-methyl-5-nitro-benzaldehyde oxime (commercially available) using an analogous procedure and was purified by column chromatography on silica gel (eluent: cyclohexane/ethyl acetate 3:1). $^1$H-NMR (CDCl$_3$, 400 MHz): 8.22 (s, 1H), 8.12 (s, 1H), 7.90 (s, 1H), 7.52 (s, 1H), 7.40 (s, 1H), 4.18 (d, 1H), 3.80 (d, 1H), 2.52 (s, 3H).

5-(3,5-Dichloro-phenyl)-3-(2-fluoro-3-nitro-phenyl)-5-trifluoromethyl-4,5-dihydro-isoxazole was made from 2-fluoro-3-nitro-benzaldehyde oxime (Example I1) using an analogous procedure and was purified by column chromatography on silica gel (eluent: cyclohexane/ethyl acetate 3:1). $^1$H-NMR (CDCl$_3$, 400 MHz): 8.25 (m, 1H), 8.16 (m, 1H), 7.54 (s, 2H), 7.47 (m, 1H), 7.44 (m, 1H), 4.24 (dd, 1H), 3.86 (dd, 1H).

Example I3

Preparation of 3-[5-(3,5-dichloro-phenyl)-5-trifluoromethyl-4,5-dihydro-isoxazol-3-yl]-phenylamine

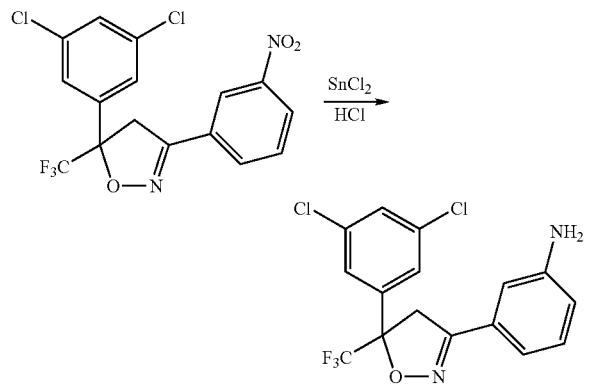

To a solution of 5-(3,5-dichloro-phenyl)-3-(3-nitro-phenyl)-5-trifluoromethyl-4,5-dihydro-isoxazole (15.0 g, 37 mmol) (Example I2) in isopropanol (120 ml) was added tin (II) chloride (25 g, 133 mmol). The mixture was cooled to 0° C. and aqueous hydrochloric acid (concentrated) (23 ml) was added slowly at 0° C. The reaction mixture was heated to 80° C. for 2 hours. Then ⅓ of the total volume of isopropanol was evaporated. Water (100 ml) was added to the mixture and aqueous sodium hydroxide (4N) was added to adjust the pH to 8-9. The aqueous phase was extracted three times with ethyl acetate (200 ml). The combined organic extracts were dried over sodium sulfate and concentrated. The residue was purified by column chromatography on silica gel (eluent: cyclohexane/ethyl acetate 1:1) to give 3-[5-(3,5-dichloro-phenyl)-5-trifluoromethyl-4,5-dihydro-isoxazol-3-yl]-phenylamine (8.1 g, 58% yield). $^1$H-NMR (CDCl$_3$, 400 MHz): 7.56 (m, 2H), 7.43 (m, 1H), 7.20 (t, 1H), 7.05 (m, 1H), 6.97 (m, 1H), 6.78 (m, 1H), 4.08 (d, 1H), 3.8 (s, 1H), 3.68 (d, 1H).

2-Bromo-5-[5-(3,5-dichloro-phenyl)-5-trifluoromethyl-4,5-dihydro-isoxazol-3-yl]-phenylamine was made from 5-(3,5-dichloro-phenyl)-3-(4-bromo-3-nitro-phenyl)-5-trifluoromethyl-4,5-dihydro-isoxazole (Example I2) using an analogous procedure. $^1$H-NMR (CDCl$_3$, 400 MHz): 7.41-7.49 (m, 4H), 7.10 (d, 1H), 6.88 (dd, 1H), 4.04 (d, 1H), 3.63 (d, 1H).

5-[5-(3,5-Dichloro-phenyl)-5-trifluoromethyl-4,5-dihydro-isoxazol-3-yl]-2-fluoro-phenylamine was made from 5-(3,5-dichloro-phenyl)-3-(4-fluoro-3-nitro-phenyl)-5-trifluoromethyl-4,5-dihydro-isoxazole (Example I2) using an analogous procedure. $^1$H-NMR (CDCl$_3$, 400 MHz): 7.52 (s, 2H), 7.43 (s, 1H), 7.18 (dd, 1H), 7.0 (t, 1H), 6.88 (m, 1H), 4.02 (d, 1H), 3.84 (s, 2H), 3.62 (d, 1H).

3-[5-(3,5-Dichloro-phenyl)-5-trifluoromethyl-4,5-dihydro-isoxazol-3-yl]-5-methyl-phenylamine was made from 5-(3,5-dichloro-phenyl)-3-(3-methyl-5-nitro-phenyl)-5-trifluoromethyl-4,5-dihydro-isoxazole (Example I2) using an analogous procedure. $^1$H-NMR (CDCl$_3$, 400 MHz): 7.52 (s, 2H), 7.40 (s, 1H), 6.86 (s, 1H), 6.82 (s, 1H), 6.60 (m, 1H), 4.08 (d, 1H), 3.75 (s, 2H), 3.70 (d, 1H), 2.3 (s, 3H).

3-[5-(3,5-Dichloro-phenyl)-5-trifluoromethyl-4,5-dihydro-isoxazol-3-yl]-2-fluoro-phenylamine was made from 5-(3,5-dichloro-phenyl)-3-(2-fluoro-3-nitro-phenyl)-5-trifluoromethyl-4,5-dihydro-isoxazole (Example I2) using an analogous procedure. $^1$H-NMR (CDCl$_3$, 400 MHz): 7.52 (m, 2H), 7.43 (m, 1H), 7.18 (m, 1H), 6.99 (t, 1H), 6.88 (m, 1H), 4.18 (d, 1H), 3.84 (s, 2H), 3.77 (d,1H).

Example I4

Preparation of 2-amino-4-[5-(3,5-dichloro-phenyl)-5-trifluoromethyl-4,5-dihydro-isoxazol-3-yl]-benzonitrile

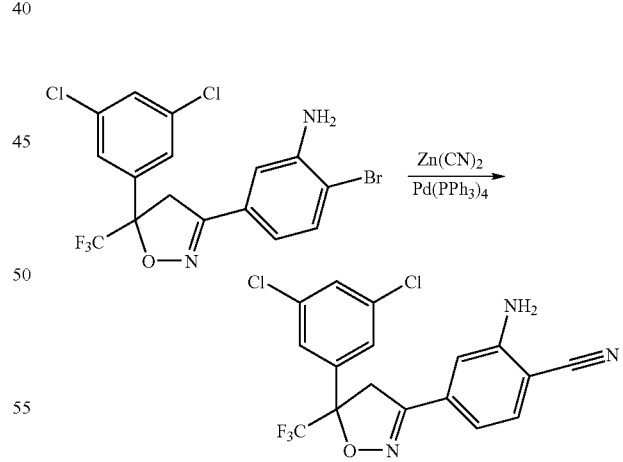

To a solution of 2-bromo-5-[5-(3,5-dichloro-phenyl)-5-trifluoromethyl-4,5-dihydro-isoxazol-3-yl]-phenylamine (Example I3) (0.840 g, 1.84 mmol) in N,N-dimethylformamide (3 ml) under a nitrogen atmosphere was added zinc(II) cyanide (0.346 g, 2.94 mmol) and tetrakis(triphenylphosphine) palladium(0) (0.255 g, 0.22 mmol). The reaction mixture was stirred at 100° C. for 16 hours. The reaction mixture was diluted with toluene and the phases were separated. The aqueous phase was extracted twice with toluene. The combined organic phases were washed with brine and aqueous ammonium hydroxide (saturated), dried over sodium sulfate and concentrated. The residue was purified by column chromatography on silica gel (eluent: ethyl acetate/cyclohexane 1:5) to give 2-amino-4-[5-(3,5-dichloro-phenyl)-5-trifluoromethyl-4,5-dihydro-isoxazol-3-yl]-benzonitrile (0.480 g, 36% yield). $^1$H-NMR (CDCl$_3$, 400 MHz): 7.45 (m, 4H), 7.08 (s, 1H), 6.95 (q, 1H), 4.52 (s, 2H), 4.02 (d, 1H), 3.62 (d, 1H).

Example I5

Preparation of 4-cyano-2-methyl-benzoic acid methyl ester

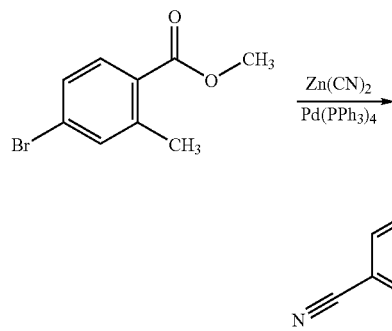

To a solution of 4-bromo-2-methyl-benzoic acid (commercially available) (108 g, 471 mmol) in N,N-dimethylformamide (4 l) under a nitrogen atmosphere was added zinc(II) cyanide (88.5 g, 753.6 mmol) and tetrakis(triphenylphosphine)palladium(0) (65 g, 56.60 mmol). The reaction mixture was stirred at 100° C. for 16 hours. The reaction mixture was diluted with toluene and the phases were separated. The aqueous phase was extracted twice with toluene. The combined organic phases were washed with brine and aqueous ammonium hydroxide (saturated), dried over sodium sulfate and concentrated. The residue was purified by column chromatography on silica gel (eluent: ethyl acetate/cyclohexane 1:5) to give 4-cyano-2-methyl-benzoic acid methyl ester (73 g, 89% yield). $^1$H-NMR (400 MHz, CDCl$_3$): 7.78 (d, 1H), 7.52 (m, 2H), 3.92 (s, 3H), 2.62 (s, 3H).

Example I6

Preparation of 4-cyano-2-methyl-benzoic acid

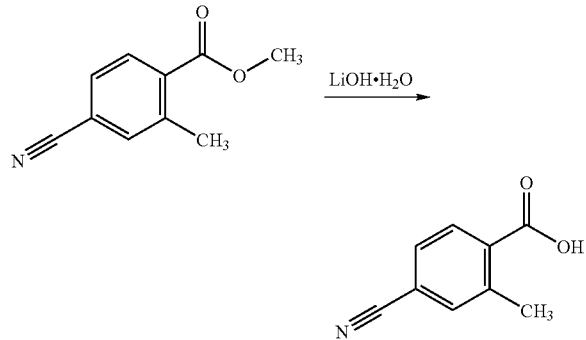

To a solution of 4-cyano-2-methyl-benzoic acid (Example I4) (61 g, 348 mmol) in a mixture of water (0.360 mL) and tetrahydrofuran (1.4 l) was added lithium hydroxide hydrate (31.4 g, 748.2 mmol). The reaction mixture was stirred at ambient temperature for 3 hours. The reaction mixture was concentrated. The residue was acidified by addition of aqueous hydrochloric acid (1N) and extracted with a mixture of methanol and chloroform (5:95). The organic phase was dried over sodium sulfate and concentrated. The residue was crystallized in a mixture of ethyl acetate and cyclohexane to give 4-cyano-2-methyl-benzoic acid (55.5 g, 99% yield). $^1$H-NMR (400 MHz, CDCl$_3$): 7.89 (d, 1H), 7.80 (s, 1H), 7.72 (d, 1H), 2.51 (s, 3H).

Example P1

Preparation of 4-cyano-N-{3-[5-(3,5-dichloro-phenyl)-5-trifluoromethyl-4,5-dihydro-isoxazol-3-yl]phenyl}-benzamide (Compound No. A4 of Table A)

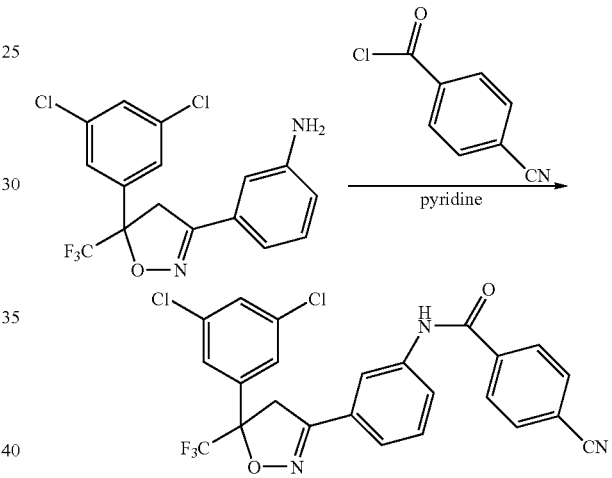

To a solution of 3-[5-(3,5-dichloro-phenyl)-5-trifluoromethyl-4,5-dihydro-isoxazol-3-yl]-phenylamine (0.300 mg, 0.79 mmol) (Example I3) in tetrahydrofuran (4 ml) was added pyridine (0.128 ml, 1.59 mmol). 4-Cyano-benzoyl chloride (0.176 g, 1 mmol) was added under vigorous stirring at ambient temperature. The reaction mixture was stirred for 3 hours at ambient temperature. Aqueous sodium hydrogen carbonate (saturated) was added and the phases were separated. The aqueous phase was extracted twice with ethyl acetate. The combined organic extracts were dried over sodium sulfate and concentrated. The residue was purified by column chromatography on silica gel (eluent: cyclohexane/ethyl acetate 2:1) to give Compound No. A4 of Table A (0.342 g, 85% yield). $^1$H-NMR (400 MHz, CDCl$_3$): 8.68 (s, 1H), 8.10 (s, 1H), 8.0 (m, 2H), 7.75 (m, 3H), 7.49 (s, 2H), 7.42 (m, 3H), 4.12 (d, 1H), 3.72 (d, 1H).

Analogous procedures were used to prepare the following compounds: Compound Nos. A1-A3 of Table A, Compound Nos. B25-B28 of Table B, Compound Nos. C$_1$-C$_4$ of Table C, Compound Nos. D1, D3 and D4 of Table D and Compound Nos. E2, E3 and E5 of Table E.

Compound No. A1 of Table A. $^1$H-NMR (400 MHz, CDCl$_3$): 8.38 (m, 2H), 8.22 (s, 1H), 8.07 (m, 3H), 7.72 (dd, 1H), 7.50-7.42 (m, 5H), 4.12 (d, 1H), 3.73 (d, 1H).

Compound No. A2 of Table A. ¹H-NMR (400 MHz, CDCl₃): 8.10 (s, 1H), 7.98 (s, 1H), 7.92 (m, 2H), 7.68 (m, 1H), 7.62-7.45 (m, 8H), 4.12 (d, 1H), 3.74 (d, 1H).

Compound No. A3 of Table A. ¹H-NMR (400 MHz, CDCl₃): 8.12 (s, 1H), 8.05 (s, 1H), 7.90 (m, 2H), 7.69 (m, 1H), 7.50-7.38 (m, 4H), 7.13 (m, 2H), 4.12 (d, 1H), 3.72 (d, 1H).

Example P2

Preparation of pentanoic acid {3-[5-(3,5-dichloro-phenyl)-5-trifluoromethyl-4,5-dihydro-isoxazol-3-yl]-phenyl}-amide (Compound No. A6 of Table A)

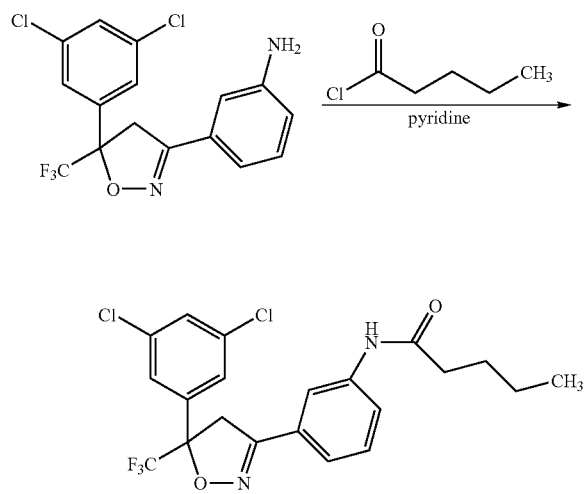

To a solution of 3-[5-(3,5-dichloro-phenyl)-5-trifluoromethyl-4,5-dihydro-isoxazol-3-yl]-phenylamine (0.150 mg, 0.40 mmol) (Example I3) in tetrahydrofuran (4 ml) was added pyridine (0.085 ml, 1.06 mmol). Pentanoyl chloride (0.063 ml, 0.53 mmol) was added under vigorous stirring at ambient temperature. The reaction mixture was stirred for 3 hours at ambient temperature. Aqueous sodium hydrogen carbonate (saturated) and ethyl acetate was added and the phases were separated. The aqueous phase was extracted twice with ethyl acetate. The combined organic extracts were dried over sodium sulfate and concentrated. The residue was purified by chromatography on silica gel (eluent: cyclohexane/ethyl acetate 2:1) to give Compound No. A6 of Table A (0.165 g, 89% yield). ¹H-NMR (400 MHz, CDCl₃): 8.00 (s, 1H), 7.70 (s, 1H), 7.53 (d, 1H), 7.49 (s, 2H), 7.42 (m, 2H), 7.35 (m, 1H), 4.09 (d, 1H), 3.72 (d, 1H), 2.40 (t, 2H), 1.70 (m, 2H), 1.40 (m, 2H), 0.94 (t, 3H).

Analogous procedures were used to prepare the following compounds: Compound Nos. A5, A7 and A8 of Table A.

Compound No. A5 of Table A. ¹H-NMR (400 MHz, CDCl₃): 7.85 (s, 1H), 7.51-7.33 (m, 9H), 7.15 (s, 1H), 4.09 (d, 1H), 3.75 (s, 2H), 3.70 (d, 1H).

Compound No. A7 of Table A. ¹H-NMR (400 MHz, CDCl₃): 8.39 (s, 1H), 7.97 (s, 1H), 7.65 (d, 1H), 7.53-7.38 (m, 5H), 4.12 (d, 1H), 4.04 (s, 2H), 3.74 (d, 1H), 3.53 (s, 3H).

Compound No. A8 of Table A. ¹H-NMR (400 MHz, CDCl₃): 8.24 (s, 1H), 7.85 (t, 1H), 7.56 (d, 1H), 7.45 (m, 3H), 7.39-7.32 (m, 2H), 4.14 (s, 2H), 4.05 (d, 1H), 3.64 (d, 1H).

Example P3

General Method for the Parallel Synthesis of Benzamides

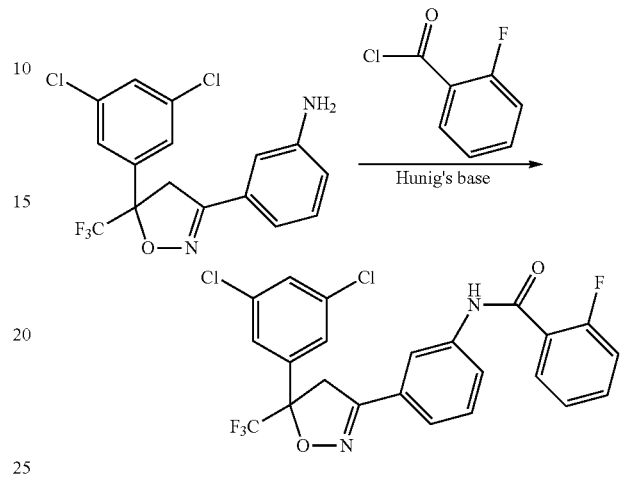

Solution A was prepared by dissolving the amino derivative (0.65 mmol), 3-[5-(3,5-dichloro-phenyl)-5-trifluoromethyl-4,5-dihydro-isoxazol-3-yl]-phenylamine (Example I3) in the case of Compound No. A9 of Table A, in toluene (7.8 ml). Solution B was prepared by dissolving the acid chloride (1 mol), 2-fluoro-benzoyl chloride in the case of Compound No. A9 of Table A, in toluene (8 ml).

Solution A (0.3 ml, 25 mmol) was put in a well and Solution B (0.4 ml, 50 mmol), and diisopropylethylamine ("Hunig's Base") (30 µl, 150 µmol) were added successively. The mixture was stirred at 55° C. for 16 hours. The solvent was evaporated and the mixture was diluted with a mixture of acetonitrile (0.6 ml) and N,N-dimethylacetamide (0.2 ml) and then purified by HPLC to give the desired compound.

This general method was used to prepare a number of compounds in parallel: Compound Nos. A9-A28 of Table A, Compound Nos. B1-B24 of Table B, Compound Nos. C1, C3 and C₅-C₂₆ of Table C, Compound Nos. D2 and D5-D24 of Table D, and Compound Nos. E1, E4 and E6-E27 of Table E.

The following methods were used for HPLC-MS analysis: Method A (Water Alliance 2795 LC): the following HPLC gradient conditions were used. Solvent A: 0.1% of formic acid in water/acetonitrile (9:1), and Solvent B: 0.1% of formic acid in acetonitrile.

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.

Method B (Agilent 1100er Series): the following HPLC gradient conditions were used. Solvent A: 0.1% of formic acid in water/acetonitrile (9:1), and Solvent B: 0.1% of formic acid in acetonitrile.

| Time (minutes) | A (%) | B (%) | Flow rate (ml/min) |
| --- | --- | --- | --- |
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C.

Method C (Waters Alliance 2795 LC): the following HPLC gradient conditions were used. Solvent A: 0.1% of formic acid in water and Solvent B: 0.1% of formic acid in acetonitrile.

| Time (minutes) | A (%) | B (%) | Flow rate (ml/min) |
| --- | --- | --- | --- |
| 0 | 80 | 20 | 1.7 |
| 2.5 | 0 | 100 | 1.7 |
| 2.8 | 0 | 100 | 1.7 |
| 2.9 | 80 | 20 | 1.7 |

Type of column: Waters atlantis dc18; Column length: 20 mm; Internal diameter of column: 3 mm; Particle Size: 3 micron; Temperature: 40° C.

Method D (Agilent 1100er Series): the following HPLC gradient conditions were used. Solvent A: 0.1% of formic acid in water, and Solvent B: 0.1% of formic acid in acetonitrile.

| Time (minutes) | A (%) | B (%) | Flow rate (ml/min) |
| --- | --- | --- | --- |
| 0 | 80 | 20 | 1.7 |
| 2.5 | 0 | 100 | 1.7 |
| 2.8 | 0 | 100 | 1.7 |
| 2.9 | 80 | 20 | 1.7 |

Type of column: Waters atlantis dc18; Column length: 20 mm; Internal diameter of column: 3 mm; Particle Size: 3 micron; Temperature: 40° C.

The characteristic values obtained for each compound were the retention time ("RT", recorded in minutes) and the molecular ion, typically the cation $(M+H)^+$ or $(M-H)^+$, as listed in Table A, Table B, Table C, Table D and Table E.

TABLE A

Compounds of formula (Ia):

(Ia)

| Comp No. | $R^1$ | RT (min) | $(M + H)^+$ | HPLC-Method |
| --- | --- | --- | --- | --- |
| A1 | 4-nitro-phenyl- | 2.12 | 522 | A |
| A2 | phenyl- | 2.09 | 477 | A |
| A3 | 4-fluoro-phenyl- | 2.12 | 495 | A |
| A4 | 4-cyano-phenyl- | 2.06 | 502 | A |
| A5 | 4-chloro-benzyl- | — | — | — |
| A6 | n-butyl- | — | — | — |
| A7 | methoxymethyl- | — | — | — |
| A8 | bromomethyl- | — | — | — |
| A9 | 2-fluoro-phenyl- | 2.10 | 495 | A |
| A10 | 2-methyl-phenyl- | 2.14 | 491 | A |
| A11 | 2-chloro-phenyl- | 2.09 | 511 | A |
| A12 | 4-methyl-phenyl- | 2.18 | 491 | A |
| A13 | 4-fluoro-2-methyl-phenyl- | 2.15 | 509 | A |
| A14 | 5-chloro-2-fluoro-phenyl- | 2.31 | 533 | A |
| A15 | 2-chloro-4-nitro-phenyl- | 2.14 | 557.8 | A |
| A16 | furan-2-yl- | 1.97 | 467 | A |
| A17 | 4-trifluoromethoxy-phenyl- | 2.29 | 561 | A |
| A18 | 4-fluoro-3-trifluoro-methyl-phenyl- | 2.26 | 563 | A |
| A19 | 4-trifluoromethyl-phenyl- | 2.26 | 545 | A |
| A20 | 2-trifluoromethoxy-phenyl- | 2.18 | 561 | A |
| A21 | 2-methoxy-phenyl- | 2.21 | 507 | A |
| A22 | 2-trifluoromethyl-phenyl- | 2.12 | 545 | A |
| A23 | 2-chloro-4-fluoro-phenyl- | 2.13 | 529 | A |
| A24 | 4-methyl-[1,2,3]-thiadiazol-5-yl- | 2.00 | 499 | A |
| A25 | 2,3-difluoro-phenyl- | 2.14 | 513 | A |
| A26 | 2,4-difluoro-phenyl- | 2.15 | 513 | A |
| A27 | 2-fluoro-5-trifluoro-methyl-phenyl- | 2.26 | 563 | A |
| A28 | 2,2,2-trichloro-ethoxy- | 2.29 | 549 | A |

Key:
s = singlet; d = doublet; t = triplet; dd = double doublet; m = multiplet.

TABLE B

Compounds of formula (Ib):

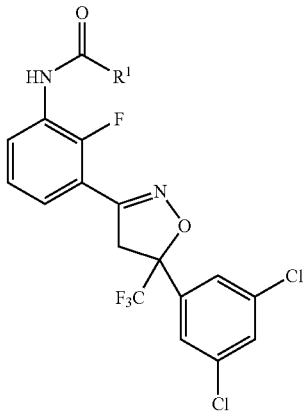

(Ib)

| Comp No. | R¹ | M.p. (° C.) | RT (min) | (M + H)⁺ | HPLC-Method |
|---|---|---|---|---|---|
| B1 | 2-fluoro-phenyl- | — | 2.49 | 515.03 | B |
| B2 | 2-methyl-phenyl- | — | 2.42 | 511.05 | B |
| B3 | 2-chloro-phenyl- | — | 2.42 | 531 | B |
| B4 | 4-cyano-phenyl- | — | 2.33 | 522.03 | B |
| B5 | 4-nitro-phenyl- | — | 2.38 | 542.02 | B |
| B6 | 4-methyl-phenyl- | — | 2.46 | 511.05 | B |
| B7 | 4-fluoro-2-methyl-phenyl- | — | 2.44 | 529.04 | B |
| B8 | 5-chloro-2-fluoro-phenyl- | — | 2.58 | 548.99 | B |
| B9 | 2-chloro-4-nitro-phenyl- | — | 2.42 | 575.98 | B |
| B10 | furan-2-yl- | — | 2.31 | 487.02 | B |
| B11 | 4-trifluoromethoxy-phenyl- | — | 2.53 | 581.02 | B |
| B12 | 4-fluoro-3-trifluoromethyl-phenyl- | — | 2.65 | 583.01 | B |
| B13 | 4-trifluoromethyl-phenyl- | — | 2.59 | 565.02 | B |
| B14 | 2-trifluoromethoxy-phenyl- | — | 2.51 | 581.02 | B |
| B15 | 2-methoxy-phenyl- | — | 2.64 | 527.05 | B |
| B16 | phenyl- | — | 2.36 | 497.04 | B |
| B17 | 4-fluoro-phenyl- | — | 2.39 | 515.03 | B |
| B18 | 2-trifluoromethyl-phenyl- | — | 2.41 | 565.02 | B |
| B19 | 2-chloro-4-fluoro-phenyl- | — | 2.44 | 548.99 | B |
| B20 | 4-methyl-[1,2,3]-thiadiazol-5-yl- | — | 2.38 | 519 | B |
| B21 | 2,3-difluoro-phenyl- | — | 2.47 | 533.02 | B |
| B22 | 2,4-difluoro-phenyl- | — | 2.5 | 533.02 | B |
| B23 | 2-fluoro-5-trifluoromethyl-phenyl- | — | 2.57 | 583.01 | B |
| B24 | 2,2,2-trichloro-ethoxy- | — | 2.54 | 566.91 | B |
| B25 | pyrid-2-yl- | 78-79 | — | — | — |
| B26 | pyrid-3-yl- | 176-177 | — | — | — |
| B27 | 2-methylthio-phenyl- | 65-67 | — | — | — |
| B28 | 4-cyano-2-methyl-phenyl- | 129-131 | — | — | — |

TABLE C

Compounds of formula (Ic):

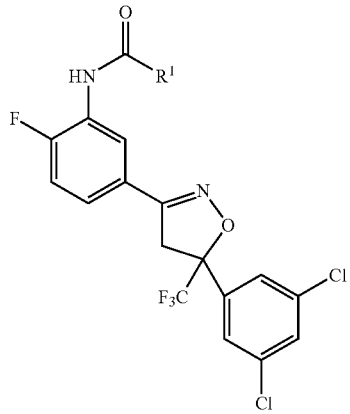

(Ic)

| Comp No. | R¹ | M.p. (° C.) | RT (min) | (M − H)⁺ | HPLC-Method |
|---|---|---|---|---|---|
| C1 | 4-cyano-phenyl- | 192-194 | 2.16 | 520.03 | C |
| C2 | 2-methyl-3-nitro-phenyl- | 208-210 | — | — | — |
| C3 | 2-chloro-4-fluoro-phenyl- | 154-156 | 2.25 | 546.99 | C |
| C4 | 4-cyano-2-methyl-phenyl- | 219-221 | — | — | — |
| C5 | 2-fluoro-phenyl- | — | 2.23 | 513.03 | C |
| C6 | 2-methyl-phenyl- | — | 2.17 | 509.05 | C |
| C7 | 2-chloro-phenyl- | — | 2.21 | 529 | C |
| C8 | 4-nitro-phenyl- | — | 2.15 | 540.02 | C |
| C9 | 4-methyl-phenyl- | — | 2.23 | 509.05 | C |
| C10 | 4-fluoro-2-methyl-phenyl- | — | 2.2 | 527.04 | C |
| C11 | 5-chloro-2-fluoro-phenyl- | — | 2.35 | 546.99 | C |
| C12 | 2-chloro-4-nitro-phenyl- | — | 2.23 | 573.98 | C |
| C13 | furan-2-yl- | — | 2.05 | 485.02 | C |
| C14 | 4-trifluoromethoxy-phenyl- | — | 2.35 | 579.02 | C |
| C15 | 4-fluoro-3-trifluoromethyl-phenyl- | — | 2.36 | 581.01 | C |
| C16 | 4-trifluoromethyl-phenyl- | — | 2.33 | 563.02 | C |
| C17 | 2-trifluoromethoxy-phenyl- | — | 2.28 | 579.02 | C |
| C18 | 2-methoxy-phenyl- | — | 2.37 | 525.05 | C |
| C19 | phenyl- | — | 2.17 | 495.04 | C |
| C20 | 4-fluoro-phenyl- | — | 2.17 | 513.03 | C |
| C21 | 2-trifluoromethyl-phenyl- | — | 2.21 | 563.02 | C |
| C22 | 4-methyl-[1,2,3]-thiadiazol-5-yl- | — | 2.0 | 517 | C |
| C23 | 2,3-difluoro-phenyl- | — | 2.23 | 531.02 | C |
| C24 | 2,4-difluoro-phenyl- | — | 2.27 | 531.02 | C |
| C25 | 2-fluoro-5-trifluoromethyl-phenyl- | — | 2.35 | 581.01 | C |
| C26 | 2,2,2-trichloro-ethoxy- | — | 2.32 | 564.91 | C |

TABLE D

Compounds of formula (Id):

(Id)

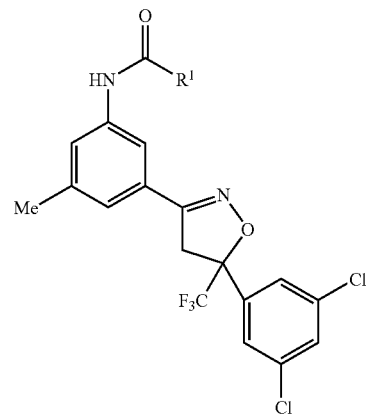

| Comp No. | R¹ | M.p. (° C.) | RT (min) | (M + H)⁺ | HPLC-Method |
|---|---|---|---|---|---|
| D1 | 4-cyano-phenyl- | 205-206 | — | — | — |
| D2 | phenyl- | — | 1.99 | 504.04 | C |
| D3 | 2-chloro-4-cyano-phenyl- | 192-194 | — | — | — |
| D4 | 4-cyano-2-methyl-phenyl- | 232-234 | — | — | — |
| D5 | 2-fluoro-phenyl- | — | 1.9 | 522.03 | C |
| D6 | 2-methyl-phenyl- | — | 2.02 | 518.06 | C |
| D7 | 2-chloro-phenyl- | — | 2.01 | 538 | C |
| D8 | 4-nitro-phenyl- | — | 1.98 | 549.03 | C |
| D9 | 4-methyl-phenyl- | — | 2.03 | 518.06 | C |
| D10 | 4-fluoro-2-methyl-phenyl- | — | 2.01 | 536.05 | C |
| D11 | 5-chloro-2-fluoro-phenyl- | — | 2.26 | 555.99 | C |
| D12 | 2-chloro-4-nitro-phenyl- | — | 2.02 | 582.99 | C |
| D13 | furan-2-yl- | — | 1.89 | 494.02 | C |
| D14 | 4-trifluoromethoxy-phenyl- | — | 2.13 | 588.02 | C |
| D15 | 4-fluoro-3-trifluoromethyl-phenyl- | — | 2.13 | 590.02 | C |
| D16 | 4-trifluoromethyl-phenyl- | — | 2.1 | 572.03 | C |
| D17 | 2-trifluoromethoxy-phenyl- | — | 2.08 | 588.02 | C |
| D18 | 4-fluoro-phenyl- | — | 2.06 | 522.03 | C |
| D19 | 2-trifluoromethyl-phenyl- | — | 2.0 | 572.03 | C |
| D20 | 2-chloro-4-fluoro-phenyl- | — | 2.02 | 555.99 | C |
| D21 | 4-methyl-[1,2,3]-thiadiazol-5-yl- | — | 1.89 | 526 | C |
| D22 | 2,3-difluoro-phenyl- | — | 2.03 | 540.02 | C |
| D23 | 2,4-difluoro-phenyl- | — | 2.08 | 540 | C |
| D24 | 2-fluoro-5-trifluoromethyl-phenyl- | — | 2.15 | 590.02 | C |

TABLE E

Compounds of formula (Ie):

(Ie)

| Comp No. | R¹ | M.p. (° C.) | RT (min) | (M + H)⁺ | HPLC-Method |
|---|---|---|---|---|---|
| E1 | 4-cyano-phenyl- | — | 2.24 | 518.06 | D |
| E2 | 2-methyl-3-nitro-phenyl- | 68-70 | — | — | — |
| E3 | 4-cyano-2-methyl-phenyl- | 97-98 | — | — | — |
| E4 | 2-chloro-4-fluoro-phenyl- | — | 2.3 | 545.01 | D |
| E5 | 2-chloro-4-cyano-phenyl- | 106-108 | — | — | — |
| E6 | 2-fluoro-phenyl- | — | 2.29 | 511.05 | D |
| E7 | 2-methyl-phenyl- | — | 2.3 | 507.08 | D |
| E8 | 2-chloro-phenyl- | — | 2.26 | 527.02 | D |
| E9 | 4-nitro-phenyl- | — | 2.27 | 538.05 | D |
| E10 | 4-methyl-phenyl- | — | 2.32 | 507.08 | D |
| E11 | 4-fluoro-2-methyl-phenyl- | — | 2.31 | 525.07 | D |
| E12 | 5-chloro-2-fluoro-phenyl- | — | 2.39 | 545.01 | D |
| E13 | 2-chloro-4-nitro-phenyl- | — | 2.29 | 572.01 | D |
| E14 | furan-2-yl- | — | 2.15 | 483.04 | D |
| E15 | 4-trifluoromethoxy-phenyl- | — | 2.43 | 577.04 | D |
| E16 | 4-fluoro-3-trifluoromethyl-phenyl- | — | 2.46 | 579.04 | D |
| E17 | 4-trifluoromethyl-phenyl- | — | 2.4 | 561.05 | D |
| E18 | 2-trifluoromethoxy-phenyl- | — | 2.32 | 577.04 | D |
| E19 | 2-methoxy-phenyl- | — | 2.36 | 523.07 | D |
| E20 | phenyl- | — | 2.24 | 493.06 | D |
| E21 | 4-fluoro-phenyl- | — | 2.27 | 511.05 | D |
| E22 | 2-trifluoromethyl-phenyl- | — | 2.26 | 561.05 | D |
| E23 | 4-methyl-[1,2,3]-thiadiazol-5-yl- | — | 2.15 | 515.02 | D |
| E24 | 2,3-difluoro-phenyl- | — | 2.28 | 529.04 | D |
| E25 | 2,4-difluoro-phenyl- | — | 2.31 | 529.04 | D |
| E26 | 2-fluoro-5-trifluoromethyl-phenyl- | — | 2.4 | 579.04 | D |
| E27 | 2,2,2-trichloro-ethoxy- | — | 2.43 | 562.94 | D |

Biological Examples

This Example illustrates the pesticidal/insecticidal properties of compounds of formula (I). Tests were performed as follows:

Spodoptera littoralis (Egyptian Cotton Leafworm):
Cotton leaf discs were placed on agar in a 24-well microtiter plate and sprayed with test solutions at an application rate of 200 ppm. After drying, the leaf discs were infested with 5 to L1 larvae. The samples were checked for mortality, feeding behavior, and growth regulation 3 days after treatment (DAT). The following compounds gave at least 80% control of Spodoptera littoralis: A1, A2, A3, A4, A6, A9, A10, A11, A12, A13, A14, A15, A16, A19, A20, A22, A23, A25, A26, A27, B1, B2, B3, B5, B6, B7, B8, B9, B11, B12, B13, B15, B16, B18, B19, B20, B21, B22, B24, B26, B27, B28, C1, C2, C3, C4, C5, C6, C7, C8, C9, C10, C12, C13, C16, C19, C20, C21, C22, C23, D1, D2, D3, D4, D5, D6, D7, D8, D9, D10, D11, D12, D13, D14, D15, D16, D17, D18, D19, D20, D21, D22, D23, D24.

Heliothis virescens (Tobacco Budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.
The following compounds gave at least 80% control of Heliothis virescens: A1, A2, A3, A4, A13, A15, A17, A19, A20, A22, A23, A25, A26, A28, B1, B2, B3, B5, B6, B7, B9, B11, B13, B15, B18, B19, B20, B21, B25, B26, B27, B28, C1, C2, C3, C4, C5, C6, C7, C8, C9, C10, C12, C14, C16, C17, C19, C20, C21, C22, D1, D2, D3, D4, D5, D6, D7, D8, D9, D10, D11, D12, D13, D14, D15, D16, D17, D18, D19, D20, D21, D22, D23, E1, E2, E3, E4, E5.

Plutella xylostella (Diamond Back Moth):
24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compounds gave at least 80% control of Plutella xylostella: A1, A3, A4, A10, A11, A15, A19, A23, A25, B1, B2, B3, B5, B6, B7, B8, B9, B11, B13, B15, B18, B19, B20, B21, B26, B27, B28, C1, C2, C3, C4, C6, C7, C8, C9, C12, C16, C19, C20, C22, D1, D2, D3, D4, D5, D6, D7, D8, D9, D10, D12, D13, D14, D15, D16, D17, D18, D19, D20, D21, D22, D23, E1, E3, E5.

Diabrotica balteata (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.
The following compounds gave at least 80% control of Diabrotica balteata: A2, A3, A4, A9, A11, A12, A13, A14, A15, A17, A19, A21, A22, A23, A24, A25, A26, B1, B2, B3, B6, B7, B8, B11, B13, B14, B15, B18, B19, B20, B21, B22, B26, B28, C1, C2, C3, C4, C5, C6, C7, C8, C9, C10, C12, C14, C15, C16, C19, C20, C21, C22, C23, C26, D1, D2, D4, D5, D6, D7, D8, D9, D10, D12, D14, D15, D16, D17, D18, D19, D20, D21, D22, D23, E2, E3, E5.

Thrips tabaci (Onion Thrips):
Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.
The following compounds gave at least 80% control of Thrips tabaci: B1, B7, B11, B15, B18, B19, B28, D1, D2, D3, D4, D5, D6, D7, D8, D9, D10, D12, D16, D18, D19, D20, D21, D23.

Tetranychus urticae (Two-Spotted Spider Mite):
Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.
The following compounds gave at least 80% control of Tetranychus urticae: A4, A9, B5, B7, B11, B28, C4, C9, C12, D1, D2, D3, D4, D6, D7, D8, D9, D10, D12, D16, D17, D18, D20, D21.

Compound Nos. A5, A7, A8 and A18 of Table A, Compound Nos. B4, B10, B17 and B23 of Table B, and Compound Nos. C11, C18, C24 and C25 of Table C were tested using the same protocols and showed little or no effect on mortality, feeding behavior, or growth regulation under the test conditions.

The invention claimed is:
1. A compound of formula (I)

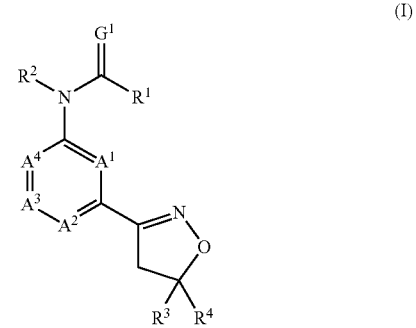

wherein
$A^1$, $A^2$, and $A^3$ are independently of one another C—H, C—$R^5$, or nitrogen, provided that no more than two of $A^1$, $A^2$, and $A^3$ are nitrogen;
$A^4$ is C—CN;
$G^1$ is oxygen or sulfur;
$R^1$ is $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, $C_1$-$C_6$alkoxycarbonyl-, aryl-$C_1$-$C_6$alkyl- or aryl-$C_1$-$C_6$alkyl- substituted by one to three $R^6$, heterocyclyl-$C_1$-$C_6$alkyl- or heterocyclyl-$C_1$-$C_6$alkyl- substituted by one to three $R^6$; or
$R^1$ is aryl or aryl substituted by one to three $R^6$, or
$R^1$ is heterocyclyl or heterocyclyl substituted by one to three $R^6$;
$R^2$ is hydrogen, $C_1$-$C_6$alkyl, $C_1$-$C_6$alkylcarbonyl-, or $C_1$-$C_6$alkoxycarbonyl-;
$R^3$ is $C_1$-$C_6$haloalkyl;
$R^4$ is aryl or aryl substituted by one to three $R^7$, or heterocyclyl or heterocyclyl substituted by one to three $R^7$;
each $R^5$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl-;
each $R^6$ is independently halogen, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio-, $C_1$-$C_6$haloalkylthio-, $C_1$-$C_6$alkylsulfinyl-, $C_1$-$C_6$haloalkylsulfinyl-, $C_1$-$C_6$alkylsulfonyl-, $C_1$-$C_6$haloalkylsulfonyl-, or $C_1$-$C_6$alkoxycarbonyl-; and each $R^7$ is independently halogen, cyano, nitro, $C_1$-$C_6$alkyl, $C_1$-$C_6$haloalkyl, $C_1$-$C_6$alkoxy, $C_1$-$C_6$haloalkoxy, or $C_1$-$C_6$alkoxycarbonyl-; or a salt or N-oxide thereof.

2. A compound according to claim 1 wherein $A^1$ is C—H or C—$R^5$.

3. A compound according to claim 1 wherein $A^2$ is C—H or C—$R^5$.

4. A compound according to claim 1 wherein $A^3$ is C—H or C—$R^5$.

5. A compound according to claim 1 wherein $G^1$ is oxygen.

6. A compound according to claim 1 wherein $R^1$ is $C_1$-$C_6$alkyl, $C_1$-$C_6$haloalkyl, $C_1$-$C_3$alkoxy-$C_1$-$C_3$alkyl-, $C_1$-$C_6$alkoxy, $C_1$-$C_6$haloalkoxy, aryl-$C_1$-$C_6$alkyl- or aryl-$C_1$-$C_6$alkyl- substituted by one to three $R^6$, aryl or aryl substituted by one to three $R^6$, or heterocyclyl or heterocyclyl substituted by one to three $R^6$.

7. A compound according to claim 1 wherein $R^2$ is hydrogen, methyl, ethyl, methylcarbonyl-, or methoxycarbonyl-.

8. A compound according to claim 1 wherein $R^3$ is chlorodifluoromethyl or trifluoromethyl.

9. A compound according to claim 1 wherein $R^4$ is aryl or aryl substituted by one to three $R^7$.

10. A compound according to claim 1 wherein each $R^5$ is independently bromo, chloro, fluoro, cyano, nitro, methyl, ethyl, trifluoromethyl, methoxy, difluoromethoxy, trifluoromethoxy, or methoxycarbonyl.

11. A method of combating and controlling insects, acarines, molluscs or nematodes which comprises applying to a pest, to a locus of a pest, or to a plant susceptible to attack by a pest an insecticidally, acaricidally, molluscicidally or nematicidally effective amount of a compound of formula (I) as defined in claim 1.

12. An insecticidal, acaricidal, molluscicidal or nematicidal composition comprising an insecticidally, acaricidally, molluscicidally or nematicidally effective amount of a compound of formula (I) as defined in claim 1.

13. An insecticidal, acaricidal, molluscicidal or nematicidal composition according to claim 12, wherein the composition contains one or more additional active ingredients.

14. A compound according to claim 1 wherein:
$A^1$, $A^2$, and $A^3$ are each C—H;
$G^1$ is oxygen; and
$R^1$ is aryl or aryl substituted by one to three $R^6$.

15. A compound according to claim 14 wherein $R^2$ is hydrogen.

16. An insecticidal, acaricidal, molluscicidal or nematicidal composition comprising an insecticidally, acaricidally, molluscicidally or nematicidally effective amount of a compound of formula (I) as defined in claim 14.

17. An insecticidal, acaricidal, molluscicidal or nematicidal composition comprising an insecticidally, acaricidally, molluscicidally or nematicidally effective amount of a compound of formula (I) as defined in claim 15.

* * * * *